United States Patent [19]  [11] 3,973,032
Leonard  [45] Aug. 3, 1976

[54] TREATMENT OF CITRUS TREE DISEASES

[75] Inventor: Chester D. Leonard, Lake Alfred, Fla.

[73] Assignee: Board of Regents, State of Florida for and on behalf of the University of Florida, Gainesville, Fla.

[22] Filed: Sept. 19, 1975

[21] Appl. No.: 615,036

[52] U.S. Cl. .................................. 424/280; 71/27
[51] Int. Cl.² .......................................... A01N 9/28
[58] Field of Search ................................... 424/280

[56] References Cited
UNITED STATES PATENTS
3,681,492  8/1972  Kotzbauer .......................... 424/280

OTHER PUBLICATIONS
Chemical Abstracts, 71: 19607r & 19608s, (1969).
Chemical Abstracts 73: 44177z, (1920).

Primary Examiner—Leonard Schenkman
Attorney, Agent, or Firm—Francis X. Murphy; Charles J. Knuth; Allen J. Spiegel

[57] ABSTRACT

The use of ascorbic acid, erythorbic acid and alkali metal and ammonium salts thereof for treatment of a destructive, widely distributed and rapidly spreading disease of citrus trees known as Young Tree Decline, is disclosed.

13 Claims, No Drawings

TREATMENT OF CITRUS TREE DISEASES

BACKGROUND OF THE INVENTION

This invention relates to the treatment of Young Tree Decline in citrus trees.

Young Tree Decline is a relatively recent and very serious disease of citrus trees, particularly the orange and grapefruit trees of the southeastern United States. Where it occurs in trees 10 or more years of age, particularly in sandy soils, it is more commonly termed "Sand Hill Decline." Other synonymous expressions for the affliction are "Rough Lemon Decline" and "Citrus Blight". As employed herein and in the appended claims, "Young Tree Decline" is intended to include these other terms.

Young Tree Decline has destroyed thousands of acres of sweet oranges and grapefruit in Florida and continues to spread rapidly. Symptoms include zinc-deficiency such as chlorosis patterns on leaves, dull green foliage, unseasonal wilt, small leaves in delayed growth flushes, progressive dieback of twigs and branches that may result in stunted trees with thinly-foliated live wood and masses of deadwood. The cause of this disease is not known.

Trees on rough lemon rootstock appear to be the most susceptible to the disease, even though trees on other commonly used rootstocks are not known to be immune to the disease. Since about 60 percent of the citrus trees in Florida are budded to rough lemon rootstock, the disease constitutes a very serious threat to the Florida citrus industry. Trees affected by Young Tree Decline may become commercially unproductive or die within a period of 4 to 24 months.

The owners of citrus groves affected by Young Tree Decline have been limited essentially to one of two choices: (1) remove and dispose of the affected trees, replacing them with healthy young trees, or (2) use the techniques of scion-rooting by girdling the affected trees a few inches above the bud union, applying a fungicide to the girdled area, piling soil around the tree to a point 6 or more inches above the girdle, keeping the soil mound intact against erosion by wind or water and also keeping the mount moist by irrigation during dry or rainless periods, to bring about growth of roots of the scion variety in the girdled area to supplement or replace the roots of the rootstock variety. Both of these choices have significant economic disadvantages.

Removal and disposal of affected trees often costs from $8 to $20 per tree, varying with tree size and distance the trees must be moved for burning or other disposal. Such removal must be followed by replacing the afflicted tree with a young healthy tree from the grower's own nursery or one bought from a commercial citrus nursery. Such young trees, scattered through the grove, must be watered frequently by tank truck during the first one or two years in the grove and hand fertilized separately from the bearing trees remaining in the grove. It may require five to ten years before the new trees will produce enough fruit to pay the cost of their purchase, planting and care up to bearing age. Where a great many trees are removed from the grove, there is a large drop in fruit production and consequently greatly reduced income from sales of fruit.

Scion-rooting has been tried by a number of growers with highly variable results. Many trees given this treatment die from various causes, such as failure to maintain the soil mound in place well above the girdle, failure to keep the soil mound moist enough for good root growth, or from the fungus disease "foot rot" developing on the tree trunk inside the mound. Many trees that survive this treatment fail to grow and/or produce fruit satisfactorily.

SUMMARY OF THE INVENTION

It has now been discovered that citrus trees afflicted with Young Tree Decline can be treated by a method which comprises applying to the foliage of said afflicted tree an effective amount of a compound selected from the group consisting of ascorbic acid, erythorbic acid, and alkali metal and ammonium salts thereof.

It has also been discovered that afflicted trees can be treated by a method comprising the administration of a compound selected from the group consisting of ascorbic acid, erythorbic acid, and alkali metal and ammonium salts thereof by means of soil injection as a supplement to the above mentioned foliage application.

In addition, compositions useful for the treatment of Young Tree Decline are further aspects of the invention.

DETAILED DESCRIPTION OF THE INVENTION

The present invention overcomes most of the disadvantages of prior methods. It makes it possible to save afflicted trees by easily applied treatments. Trees showing moderate to moderately-severe Young Tree Decline symptoms can be restored to vigorous growth of new leaves, resulting in greatly increased density of tree canopy or leaf cover. This improvement also results in greatly improved bloom and set of fruit along with the spring flush of growth. There is, therefore, no long waiting period of five or more years to harvest crops of fruit, as is necessary after removal of diseased trees and their replacement by new young trees.

Afflicted trees treated in accordance with the method of this invention recover more rapidly than trees treated by scion-rooting. Diseased trees restored to production can be maintained after the initial treatment by a supplemental treatment each year.

Two general methods of treatment are suitable for use, namely, application of a foliar spray and application of a soil injection, followed by a foliar spray. Descriptions of both methods of application are given below.

Foliar sprays for control of Young Tree Decline in citrus trees can be applied with one of several types of power sprayers, including those with pressure hose and spray gun, boom-type sprayers and air-blast sprayers. The spray solution should be applied to the point of run-off from the leaves, that is, both sides of all leaves should be wet.

The application of a soil injection requires the use of a soil injector which can be made from one-half inch galvanized water pipe, with a 3-foot length of pipe as the vertical section, and a horizontal handle fastened to the vertical section with a T-joint. One end of the handle is suitable 6 to 8 inches long, with the outer end closed by a steel cap. The other end of the handle has a hose fitting to which a spray hose is attached to deliver the solution from a sprayer tank under pressure, e.g. 100 to 130 psi. A quick on-off valve is installed in the handle near the hose fitting. A small $5/8 \times 3/4$ inch water meter installed in the handle between the quick on-off valve and the vertical pipe will provide accurate measurement of the volume of solution injected into the soil around each tree. A perforated flat iron cap is threaded onto the bottom of the vertical pipe. For use on soils classified as sands or fine sands, three holes each 3/32-inch in diameter, bored through the bottom of the cap at an angle of about 45 degrees, are satisfactory. Penetration of the injector pipe into the soil is accomplished almost entirely by the solution pressure and requires little or no downward pressure on the handle, by the operator. The 45° angle provides good distribution of the treatment solution in the top 12 to 18 inches of soil around the injection point. For soils heavier in texture, the holes are preferably bored at an angle of about 10° to 20° from the vertical, for easy soil penetration. The soil injection is made by attaching the spray hose to the injector, opening the spray valve, turning on the pump pressure (adjusted to about 100 to 130 psi), opening the quick on-off valve of the injector handle and inserting the vertical portion of the injector into the soil to a depth of 9 to 12 inches. The soil injections are best made in a zig-zag circle around the tree from about 3 to 7 feet from the tree trunk, depending on the size of the tree canopy. As soon as the solution is seen to emerge from the soil surface around the injector, the injector is removed from the soil and inserted at a point 2 or 3 feet from the first point of penetration. This procedure is continued around the tree.

As active ingredients, ascorbic cid, erythorbic acid and alkali metal and ammonium salts thereof are effective in controlling Young Tree Decline when applied in aqueous solutions to the trees. The preferred compounds are sodium ascorbate and sodium erythorbate.

The spray composition contains from about 1 to 4% w/v of active ingredient, with the preferred range being from 1 to 3% w/v. It also preferably contains from about 0.6 to 1% w/v calcium nitrate, as a source of calcium. Urea is also preferably present in a concentration of about 0.6 to 1% w/v as a nitrogen source. It is also desirable that a non-ionic surfactant be included in the spray composition, since the citrus leaf is waxy in nature and the surfactant will aid the thorough application of the compound to the leaf. The surfactant is ordinarily used in a concentration of about 0.1 to 0.5% w/v, with the preferred range being 0.25 to 0.5% w/v.

The surfactants of choice are polyethylene glycol dodecyl ether, e.g. Tergitol TMN-6 (Union Carbide Corp.) and Surfactant WK (E. I. DuPont De Nemours & Company, Inc.), and polyethylene glycol octylphenyl ether, e.g. Triton X-363-M (Rohm and Haas Company).

The soil injection composition contains from about 1 to 6% w/v of active ingredient, with the preferred concentration being from about 2.5 to 3.5% w/v. Calcium nitrate or calcium chloride is also preferably included, in the amount of from about 1 to 5% w/v. Urea is also desirably included, in a concentration of from about 0.3 to 1% w/v.

The active ingredient is applied at a level of from about 0.5 kg. to 10 kg. per tree depending on the size of the tree and the severity of the Young Tree Decline.

An afflicted tree receives 7 to 12 gallons of spray solution depending on the severity of the Young Tree Decline. Therefore, if a 2.5% solution of sodium erythorbate is used, approximately 0.7 kg. (1.5 lbs.) to 1.4 kg. (3 lbs.) is applied per tree.

If the tree also receives a soil injection, (usual amount is 15 gallons per tree) 1.6 kg. (3.5 lbs.) of sodium erythorbate is used. For large trees, 25 gallons per tree is applied and 2.1 kg. (4.6 lbs.) of sodium erythorbate is used.

Therefore, depending on tree size and severity of Young Tree Decline, trees receiving a combination of foliar spray plus soil injection will receive from 2.3 kg. (5.0 lbs.) to 3.5 kg. (7.7 lbs.) of sodium erythorbate per tree. For a tree suffering from the beginning symptoms of Young Tree Decline, treatment by foliar spray is usually adequate. For a tree afflicted with severe symptoms of Young Tree Decline, a soil injection plus a foliar spray is best. In both instances at least one additional spray should be applied at the start of the next year after treatment. Timing of treatment is significant and treatment should preferably commence at the start of the spring flush. The best time for treatment is a week or two prior to the spring flush of growth or very early in the spring flush. However, treatment can also be applied when the tree is dormant, i.e. in December.

In some of the following illustrative examples, the trees were examined and given "Young Tree Decline (YTD) ratings" as follows: 0 = apparently healthy with no recognizable decline symptoms; 0.5 = early stage of the decline with a few clusters of leaves with zinc deficiency-like chlorosis patterns; 1 = considerable thinning of foliage and presence of small and medium-size deadwood; 1.5 = thinner foliage than YTD No. 1 rated tree with increased size and number of dead branches; 2 = relatively thin foliage all over the tree with more deadwood than a YTD No. 1.5 rated tree; 2.5 and 3 = severe decline, with very thin foliage and very prominent deadwood.

The following examples are provided for illustrative purposes and should not be interpreted as limiting the invention, the scope of which is defined by the appended claims.

EXAMPLE 1

Nine orange trees having an average initial YTD rating of 1.3 were each treated in early February with approximately 15 gal. (56.8 l) of the following aqueous composition by means of soil injection:

|  | Per 100 gal. solution (378.5 l) |
|---|---|
| Sodium erythorbate | 23 lb. (2.8% w/v) |
| Urea | 4 lb. (0.5% w/v) |
| Calcium nitrate | 40 lb. (5.0% w/v) |

These trees were also each treated with approximately 7 gal. (26.5 l) of an aqueous foliar spray composition:

|  | Per 100 gal. solution (378.5 l) |
|---|---|
| Sodium erythorbate | 14 lb. (1.5% w/v) |
| Urea | 5 lb. (0.6% w/v) |
| Calcium nitrate | 5 lb. (0.6% w/v) |
| Tergitol TMN-6 (Union Carbide Corp.) | 2 pts. (0.25% w/v) |

At the end of July eight trees show improvement and one did not. The average YTD rating was 0.8.

EXAMPLE 2

Eleven orange trees having an average initial YTD rating of 1.8 were each treated with a soil injection and foliar spray in early February as described in Example 1. Additionally in mid-May of the same year each of these trees received a second application by soil injection, approximately 15 gal., (56.8 l) and foliar spray, approximately 7 gal., (26.5 l):

| Soil Injection | Per 100 gal. solution(378.5 l) |
|---|---|
| Sodium erythorbate | 35 lb. (4.2% w/v) |
| Urea | 4 lb. (0.5% w/v) |
| Calcium nitrate | 40 lb. (5.0% w/v) |
| Tergitol TMN-6 (Union Carbide Corp.) | 2 pts. (0.25% w/v) |
| Foliar Spray | Per 100 gal. solution(378.5 l) |
| Sodium erythorbate | 23 lb. (2.8% w/v) |
| Urea | 5 lb. (0.6% w/v) |
| Calcium nitrate | 5 lb. (0.6% w/v) |
| Tergitol TMN-6 (Union Carbide Corp.) | 2 pts. (0.25% w/v) |

At the end of July all eleven trees showed improvement. The average YTD rating was 1.2.

EXAMPLE 3

Forty-seven orange trees having an average YTD rating of 0.6 were each treated with approximately 7 gal. of foliar spray in late February:

| | Per 100 gal. solution(378.5 l) |
|---|---|
| Sodium erythorbate | 23 lb. (2.8% w/v) |
| Urea | 5 lb. (0.6% w/v) |
| Calcium nitrate | 5 lb. (0.6% w/v) |
| Tergitol TMN-6 (Union Carbide Corp.) | 2 pts. (0.25% w/v) |

At the end of July, 32 trees had improved, 11 remained the same and 4 had declined further. The average YTD rating was 0.4.

EXAMPLE 4

Thirty-four orange trees having an average initial YTD rating of 0.8 were each treated with a foliar spray in early February as described in the preceding example. Additionally in mid-May of the same year each of these trees received a second application of 7 gal. of a foliar spray:

| | Per 100 gal. solution(378.5 l) |
|---|---|
| Sodium erythorbate | 23 lb. (2.8% w/v) |
| Urea | 8 lb. (1.0% w/v) |
| Tergitol TMN-6 (Union Carbide Corp.) | 3 pts. (0.4% w/v) |

At the end of July, 25 trees had improved, 5 remained the same, and 4 declined. The average YTD reading was 0.5.

EXAMPLE 5

Thirty-four trees having a YTD rating of 0.8 were untreated and used as controls for the foregoing tests. At the end of July, 10 trees showed improvement, 10 remained the same, and 14 declined. The average YTD reading was 0.9.

The results of Examples 1–5 demonstrate that sodium erythorbate treatments consistently improved YTD afflicted trees. Only 8 of the 101 treated trees declined further while 76 improved significantly after treatment. Fourteen of the 34 control trees declined further, with 10 trees rated as improved without treatment.

EXAMPLE 6

Comparable results are obtained by the use of ascorbic acid, erythorbic acid, sodium ascorbate, potassium ascorbate or potassium erythorbate as a replacement for the sodium erythorbate used in Examples 1 to 4.

EXAMPLE 7

Two groups of four Marsh grapefruit trees with YTD ratings of 1.5 received a single foliar spray (approximately 7 gal.) of a 1.5% w/v solution of sodium erythorbate and sodium ascorbate respectively, during the summer. The spray also contained 1.2% w/v of urea and 0.13% w/v of Plyac (Allied Chemical Corp.) Although there was only slight improvement in the condition of these trees during the rest of the year, they improved rapidly in the late winter and early spring of the next year, when the spring flush of growth emerged. In this instance the Young Tree Decline rating was supplemented by making 48 measurements of percent of full sunlight passing through the canopy of the tree and reaching the ground within an annular area between 1 and 4½ ft. from the trunk. The light meter used was modified by replacing the microcoulometer with a 0–100 microammeter having a Lifelite F-75 filter. A ⅝-inch black plastic chimney around the photocell and extending 1½ inches above it screened out light from the sides, limiting the light measured to that entering through the canopy from above the tree within a vertical angle of 39°. The 48 measurements were made around the tree. The meter was set to read 100 in full sunlight before each series of 12 readings. The measurements were taken between 10 a.m. and 3 p.m. on both diseased and apparently healthy trees. The significance of the light data was measured by analysis of variance and Duncan's Multiple Range Test.

The mean light measurements for both treatments showed significant improvement of canopy density over the YTD control treatment:

| | YTD Rating After Treatment | Full Sunlight Under Tree Canopy |
|---|---|---|
| Control | 1.5 | 84% |
| Sodium erythorbate | 0.69 | 60% |
| Sodium ascorbate | 0.66 | 60% |

EXAMPLE 8

The following spray solution was prepared:

| Ingredients | Per 100 gal. solution(378.5 l) |
|---|---|
| Sodium erythorbate | 23 lb. (2.8% w/v) |
| Urea | 5 lb. (0.6% w/v) |
| Calcium nitrate | 5 lb. (0.6% w/v) |
| Tritol X-363-M (Rohm and Haas Co.) | 2 pts. (0.25% w/v) |

Six orange trees afflicted with Young Tree Decline were sprayed with approximately 7 gallons each of the above mixture until the leaves were thoroughly wet. At the end of 18 days considerable new young leaves were starting.

Six orange trees afflicted with Young Tree Decline were sprayed as above, but with the spray solution containing 0.4% w/v of Triton X-363-M (Rohm and Haas Co.). At the end of 18 days there was considerable new spring flush with more full grown leaves than above.

Four orange trees afflicted with Young Tree Decline were sprayed as above, but with the spray solution containing 0.5% w/v of Triton X-363-M (Rohm and Haas Co.). At the end of 18 days there was considerable full size spring flush and a moderate amount of new flush starting to grow.

Three orange trees afflicted with Young Tree Decline were untreated and at the end of 18 days showed little or no new growth.

EXAMPLE 9

Three orange trees afflicted with Young Tree Decline were treated with 15 gallons of the following soil injection composition:

| Ingredients | Per 100 gal. solution (378.5 l) |
|---|---|
| Sodium erythorbate | 35 lb. (4.2% w/v) |
| Urea | 4 lb. (0.5% w/v) |
| Calcium nitrate | 4 lb. (0.5% w/v) |

The following solution was prepared and also applied to the trees by foliar spray:

| Ingredients | Per 100 gal. solution (378.5 l) |
|---|---|
| Sodium erythorbate | 20 lb. (2.4% w/v) |
| Urea | 5 lb. (0.6% w/v) |
| Calcium nitrate | 5 lb. (0.6% w/v) |
| Triton X-363-M (Rohm and Haas Co.) | 2 pts. (0.25% w/v) |

At the end of one month extensive new small twigs were starting.

Three orange trees afflicted with Young Tree Decline were treated as above but with 44 lbs. (5.3% w/v) per 100 gallons of calcium nitrate used in the soil injection composition. At the end of one month a considerable number of new twigs were starting.

The use of calcium chloride instead of calcium nitrate in the above soil injection compositions produces comparable results.

EXAMPLE 10

Four orange trees afflicted with Young Tree Decline were given a soil injection of 10 gallons per tree of the following:

| Ingredients | Per 100 gal. solution (378.5 l) |
|---|---|
| Sodium erythorbate | 35 lb. (4.2% w/v) |
| Urea | 8 lb. (1% w/v) |

The trees were also each sprayed with approximately 7 gallons of the following spray solution immediately after soil injection:

| Ingredients | Per 100 gal. solution (378.5 l) |
|---|---|
| Sodium erythorbate | 23 lb. (2.8% w/v) |
| Urea | 5 lb. (0.6% w/v) |
| Calcium nitrate | 5 lb. (0.6% w/v) |
| Triton TMN-6 (Rohm and Haas Co.) | 2 pts. (0.25% w/v) |
| Plyac (Allied Chemical Corp.) | 6 pts. (0.75% w/v) |

At the end of one month heavy new leaf growth was noted.

Four afflicted orange trees were treated as above with the exception that 50 lbs. per 100 gallons (6%) of sodium erythorbate was present in the soil injection composition. At the end of one month extra thick new young twigs appeared on the branches and wood.

Four afflicted orange trees were given 15 gallons per tree of the following soil injection composition:

| Ingredients | Per 100 gal. solution (378.5 l) |
|---|---|
| Sodium erythorbate | 23 lb. (2.8% w/v) |
| Urea | 4 lb. (0.5% w/v) |
| Calcium nitrate | 40 lb. (5.0% w/v) |

The trees were also sprayed as above, and at the end of one month a heavy new growth of leaves was apparent.

EXAMPLE 11

Results comparable to those of Example 1 are obtained by treating orange trees afflicted with Young Tree Disease with approximately 15 gal. (56.8 l) of an aqueous soil injection composition containing 1% w/v of sodium ascorbate, 1% w/v or urea and 1% w/v of calcium nitrate.

The trees are also treated with approximately 7 gal. (26.5 l) of an aqueous foliar spray composition containing 4% w/v of sodium ascorbate, 1% w/v of urea, 1% w/v of calcium nitrate and 0.1% w/v of Tergitol TMN-6 (Union Carbide Corp.).

The use of 0.3% w/v urea in the above soil injection also produces comparable results.

EXAMPLE 12

Results comparable to those of Example 3 are obtained by treating afflicted orange trees with approximately 7 gal. (26.5 l) of an aqueous foliar spray composition containing 1% w/v of sodium ascorbate, 1% w/v of urea, 1% w/v of calcium nitrate and 0.50% w/v of Tergitol TMN-6 (Union Carbide Corp.).

What is claimed is:

1. A method of treating a citrus tree afflicted with Young Tree Decline which comprises applying to the foliage of said afflicted tree an effective amount of a compound selected from the group consisting of ascorbic acid, erythorbic acid and alkali metal and ammonium salts thereof.

2. The method of claim 1 wherein said compound is applied at a level of from about 0.5 kg. to 10 kg. per tree.

3. The method of claim 1 wherein said compound is sodium ascorbate.

4. The method of claim 1 wherein said compound is sodium erythorbate.

5. The method of claim 1 wherein said compound is also administered to said afflicted tree by means of soil injection as a supplement to said foliage application.

6. A foliar spray composition useful for the treatment of Young Tree Decline comprising an aqueous solution of from about 1 to 4% w/v of a compound selected from the group consisting of ascorbic acid, erythorbic acid and alkali metal and ammonium salts thereof; from about 0.6 to 1% w/v of urea; from about 0.6 to 1% w/v of calcium nitrate; and from about 0.1 to 0.5% w/v of nonionic surfactant.

7. The composition of claim 6 wherein said surfactant is polyethylene glycol dodecyl ether.

8. The composition of claim 6 wherein said surfactant is polyethylene glycol octylphenyl ether.

9. The composition of claim 6 wherein said compound is sodium erythorbate.

10. The composition of claim 6 wherein said compound is sodium ascorbate.

11. A soil injection composition useful for the treatment of Young Tree Decline comprising an aqueous solution of from about 1 to 6% w/v of a compound selected from the group consisting of ascorbic acid, erythorbic acid and alkali metal and ammonium salts thereof; from about 0.3 to 1% w/v of urea; and from about 1 to 5% w/v of calcium nitrate or calcium chloride.

12. The composition of claim 11 wherein said compound is sodium erythorbate.

13. The composition of claim 11 wherein said compound is sodium ascorbate.

* * * * *